Figure 1:
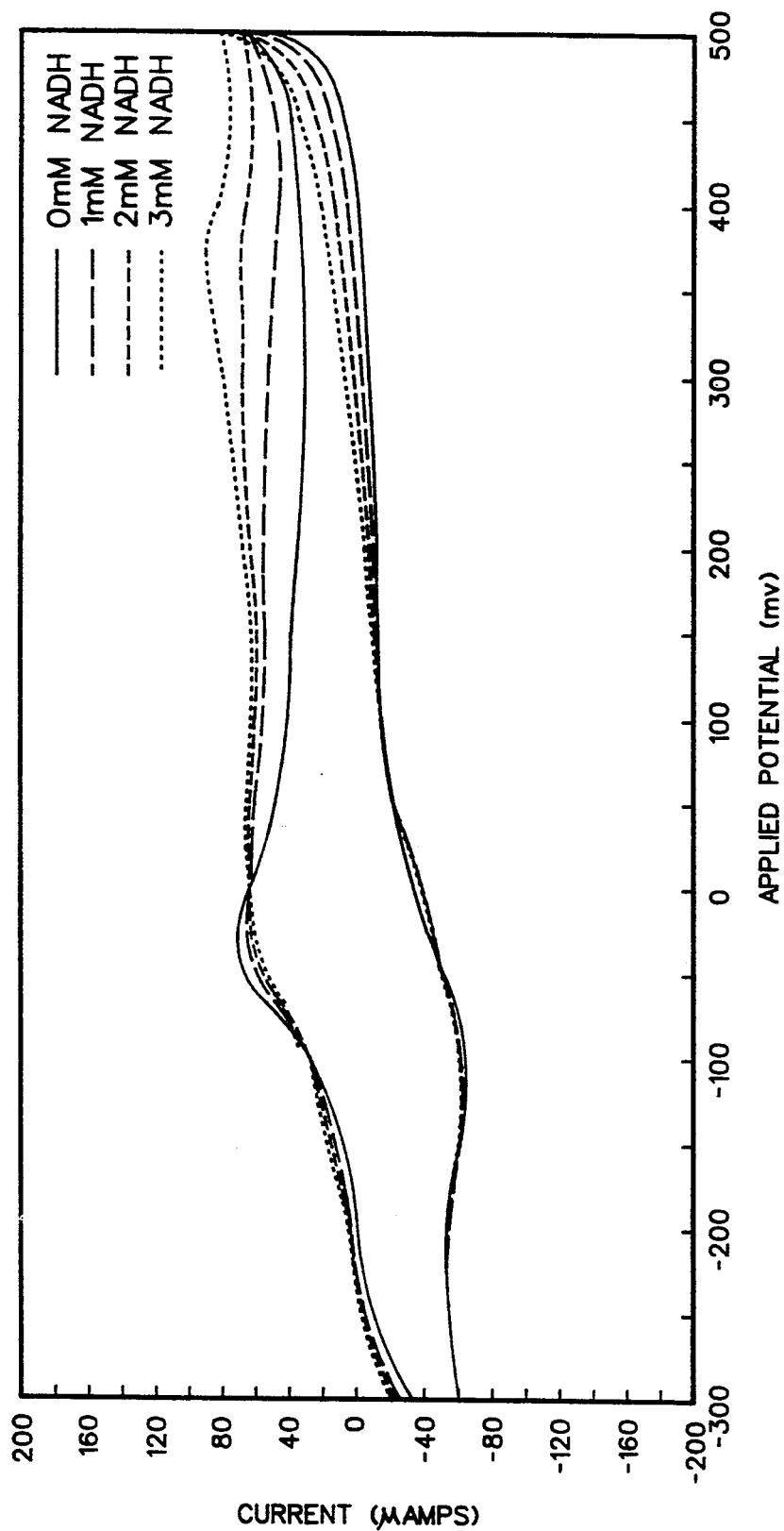

United States Patent [19]

Corey et al.

[11] Patent Number: 5,393,615
[45] Date of Patent: Feb. 28, 1995

[54] MEDIATORS SUITABLE FOR THE ELECTROCHEMICAL REGENERATION OF NADH, NADPH OR ANALOGS THEREOF

[75] Inventors: Paul F. Corey, Elkhart; Matthew K. Musho, Granger, both of Ind.

[73] Assignee: Miles Inc., Elkhart, Ind.

[21] Appl. No.: 190,855

[22] Filed: Feb. 3, 1994

[51] Int. Cl.⁶ .................. H01M 4/86; H01M 10/44
[52] U.S. Cl. .................................. 429/43; 429/50; 204/403; 204/418; 204/290 R
[58] Field of Search ............ 204/403, 418, 290 R; 435/877, 888; 429/43, 50

[56] References Cited

U.S. PATENT DOCUMENTS 4,490,464  12/1984  Gorton et al. .................. 435/817
4,810,636   3/1989  Corey ............................. 435/14

Primary Examiner—Kathryn Gorgos
Attorney, Agent, or Firm—Jerome L. Jeffers

[57] ABSTRACT

Disclosed is the use of 9H-acridin-2-one and 11H-dibenz-[b,f][1,4]oxazepin-8-one compounds as mediators suitable for the electrochemical regeneration of the co-enzymes dihydronicotinamide adenine dinucleotide (NADH), dihydronicotinamide adenine dinucleotide phosphate (NADPH) or analogs thereof.

10 Claims, 3 Drawing Sheets

MEDIATORS SUITABLE FOR THE ELECTROCHEMICAL REGENERATION OF NADH, NADPH OR ANALOGS THEREOF

BACKGROUND OF THE INVENTION

Analytical methods that combine the selectivity of enzymes with the sensitivity of amperometric detection are of interest to the diagnostic industry. The reduction of the nicotinamide co-enzymes (NAD and NADP) is particularly important because they are produced in reactions catalyzed by dehydrogenases. Dehydrogenase catalyzed reactions according to the equation:

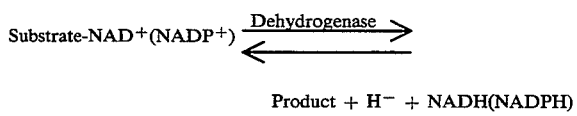

play an important role in biological cells and analytical reactions. Several hundred different dehydrogenases are known which selectively catalyze the conversion of different substrates into products. When the substrate is oxidized, the coenzymes NAD+ and NADP+ are reduced to NADH and NADPH respectively. These co-enzymes are a necessary element in the reaction due to their ability to act with the enzymes to form an energy-transferring redox couple.

The co-enzymes NAD+ and NADP+ are expensive chemicals making their regeneration by reoxidation to their original state imperative if they are to be economically used in low cost, disposable, analytical devices. The NADH is oxidized directly at different base electrode materials only with high overvoltages on the order of 1 volt. However, a decrease in this over-voltage can be obtained by the immobilization of functionalities on the electrode surface which mediate the electron transfer from NADH to the electrode. Such mediators are typically selected from materials which may be reoxidized electrochemically without excessive overvoltages rendering them useful as an auxiliary system for electrochemical regeneration. Various mediator compounds suitable for this purpose are known. In U.S. Pat. No. 4,490,464 there are mentioned, by way of background, mediators such as phenazine methosulphate (PMS); phenazine ethosulphate (PES); thionine and 1,2-benzoquinone. This patent goes on to describe electrodes which are modified to catalyze the oxidation of NADH, NADPH or analogs thereof by imparting to the electrode surface as mediator a condensed aromatic ring system comprising at least three and preferably four or more condensed aromatic rings with or without heteroatoms. More particularly, this reference describes the electron exchange with the co-enzyme or analog thereof by structural elements comprising one of either alkyl phenazinium ions, phenazinium ions, phenazinones, phenoxazinium ions, phenoxazinones, phenothiazinium ions or phenothiazinones.

Fulty et al provide a literature review of various mediators, which they describe as "electron shuttles", which provide redox coupling between the electrode and the redox center of the co-enzyme in Analytical Chimica Acta. 140 (1982) Pp. 1–18. Perhaps the best known mediators for use on graphite electrodes are phenothiazinium and phenoxazinium salts such as Meldola's Blue (II):

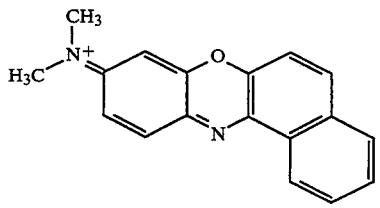

In J. Electroanal. Chem., 287 (1990) Pp. 61–80, there is described a chemically modified graphite electrode for oxidation of reduced NAD based on the phenothiazine derivative 3-β-naphthoyl-toluidine blue O (III):

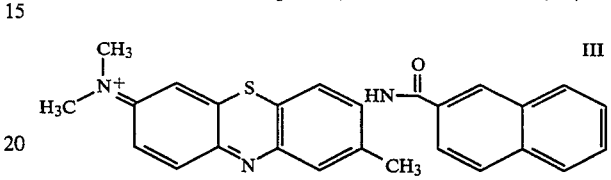

Persson et al have published a comparative study of some 3,7-diaminophenoxazine derivatives for the electrocatalytic oxidation of NADH in J. Electroanal Chem., 292 (1990) 115–138.

In U.S. Pat. 4,810,636, there are described 7-hydroxy-9H-acridin-2-one chromagens which have been derivatized at the 7-hydroxy position with an enzymatically cleavable group and substituted at the 9-position with alkyl or aryl groups.

SUMMARY OF THE INVENTION

The present invention involves an electrode suitable for the electrochemical regeneration of the co-enzymes dihydronicotinamide adenine dinucleotide (NADH), dihydronicotinamide adenine dinucleotide phosphate (NADPH) or analogs thereof, said electrode having imputed on its surface a mediator function comprising one or more substituted or unsubstituted 9-H-acridin-2-one or 11H-dibenz-[b,e][1,4oxazepine-2-one compounds.

DESCRIPTION OF THE INVENTION

This invention is predicated on the discovery that 7-hydroxy-9,9-dimethyl-9H-acridin-2-one (I) and its derivatives are useful as mediators for the electrochemical regeneration (oxidation) of NADH at an electrode.

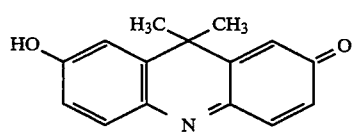

Nicotinamide adenine dinucleotide (oxidized form, NAD+; reduced form, NADH) is the cofactor providing chemical redox function for many dehydrogenase enzymes. This cofactor is reduced during the course of the enzymatic reaction as the substrate molecule is oxidized. Amperometric biosensors seeking to use these enzymes as a means to measure substrate concentration correlate this concentration with the current generated as the cofactor is electrochemically re-oxidized. The NADH can be electrochemically re-oxidized on graphite, pyrolytic carbon, glassy carbon, platinum or gold electrodes without a mediator, but this reaction occurs with several difficulties including a large overpotential and electrode fouling.

The present invention describes the first use of the acridinone class of chromogens in the electrochemical regeneration of NADH and NADPH coenzymes or their derivatives and accordingly, encompasses a wide variety of acridinone derivatives. Derivatives of NADH and NADPH such as in the case where the coenzyme is attached to a polymer are described by Dolabdjian, et al in *Enzyme Engineering Vol. 4*, G. B. Brown and G. Manecke, eds., Plenum Press, New York, 1978, Pp. 399–400 or covalently attached to the dehydrogenase enzyme as described by M. Persson, et al in *Biotechnology* 9, Pp. 280–284 (1991) or synthetic analogs bearing other substituents so long as they function as a cofactor for the dehydrogenase enzyme.

The acridinones preferred for use as mediators in the present invention can be represented by the following formula (A):

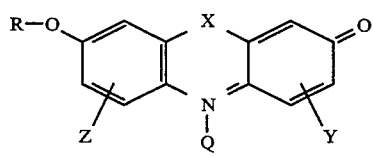

These compounds are prepared by known methods which are more fully described hereinafter. In the above formula, X represents

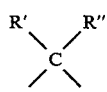

where R' and R" are independently lower alkyl of 1 to 6 carbon atoms or

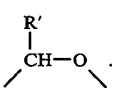

with R' being as defined above, Y and Z are independently H or another monovalent substituent, Q is $(\rightarrow O)_n$ where n=0 or 1 and R is H or lower alkyl of 1 to 6 carbon atoms. It will be evident that the aromatic rings can bear a variety of substituent groups, which do not adversely affect their electron transport properties, without departing from the scope of the present invention. Such substituent groups are limited only by the ability of one of ordinary skill in this art to prepare stable compounds which have the electrochemical properties necessary for electron transport and include such groups as substituted or unsubstituted aryl, alkoxy, aryloxy, halo (e.g. fluoro, chloro, bromo), nitro, substituted amino, such as dialkylamino, keto, carboxy, alkoxycarbonyl and amido.

The synthesis of 7 analogs of compound A whose structures are set out as formulae I and IV–IX is described in the following examples:

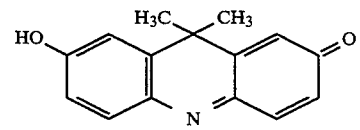

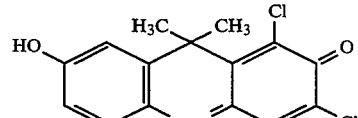

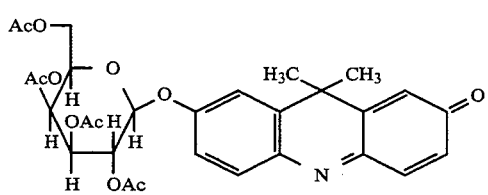

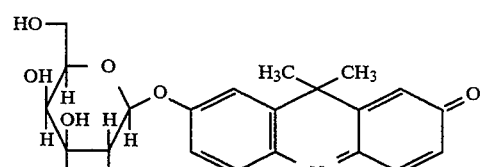

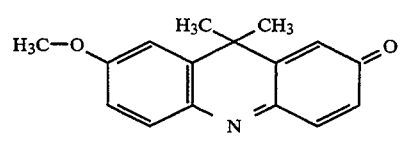

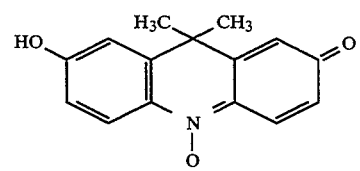

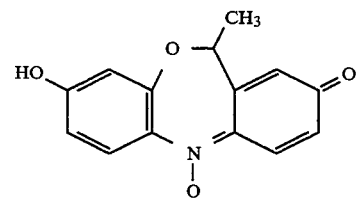

EXAMPLE I

Synthetic procedures or references to synthesis of the present compounds are as follows:

Compounds I and IV–VI

The synthesis of these compounds is described in U.S. Pat. No. 4,810,636, the disclosure of which is incorporated herein by reference.

Compound IX

The synthesis of this compound, known in the literature as "Methyl Purple", is described by Hill et al in *New Phytology* 77, 1–9 (1976), incorporated herein by reference.

Compound VII; 7-methoxy-9,9-dimethyl-9H-acridin-2-one was synthesized as follows:

Initially, 0.88 g of 60% NaH in oil (22 m mol, 1.1 eq.) was washed twice with 20 mL portions of n-pentane. The oil free NaH was suspended at room temperature in 50 mL of anhydrous dimethylformamide (DMF) and treated portionwise with 4.78 g (20 m mol, 1.0 eq.) of 7-hydroxy-9,9-dimethyl-9H-acridin-2-one (I) under an inert gas atmosphere. During this addition the mixture turned dark blue in color, evolved gas and became somewhat turbid. After about 10 minutes, 1.6 mL of CH$_3$I (25 m mol, 1.25 eq.) was added whereupon the reaction was allowed to stir at room temperature for 70 minutes. The reaction mixture was then blended into 500 mL of H$_2$O and 100 mL ethyl acetate (EtOAc), basified with 5% aqueous NaHCO$_3$ and the phases separated. The organic phase was washed twice with 5% aqueous NaHCO$_3$ and twice with brine, then dried (Na$_2$SO$_4$) and concentrated in vacuo until crystals began to form. The mixture was then heated to a boil, diluted with an equal volume of n-hexane ($\simeq$20 mL) and allowed to cool. The crystals that were deposited were isolated by filtration, washed with EtOAc/hexane (1:1) and vacuum dried to give the title compound (4.8 g, 94% yield) as rusty-red chunky prisms in two crops, with mp=140°-1° C.

Analysis

IR (CHCl$_3$)cm$-1$ 1632, 1614, 1569, 1504, 1462, 1431, 1315, 1290, 1243, 1037, 898, 818; $^1$H NMR (CDCl$_3$) δ7.64 (d, J=8.7Hz, 1H), 7.39 (d, J=7.9Hz, 1H), 7.03 (d, J=2.7Hz, 1H), 6.91 (d of d, J$_A$=2.7 Hz and J$_B$=8.7 Hz, 1H), 6.60–6.67 (m, 2H), 3.90 (s, 3H), 1.54 (s, 6H); $^{13}$C NMR (CDCl$_3$) ppm 187.1, 161.9, 150.4, 147.6, 141.7, 139.6, 136.8, 133.8, 131.0, 127.3, 112.4, 112.3, 55.6, 37.4, 32.4.

Anal. Calcd. for C$_{16}$H$_{15}$NO$_2$: C, 75.87; H, 5.97; N, 5.53. Found: C, 75.91; H, 6.07; N, 5.47.

Compound VIII; 7-methoxy-9,9-dimethyl-9H-acridin-2-one-N-oxide was synthesized as follows:

A solution of 0.2533 g (1 m mol) 7-methoxy-9,9-dimethyl-9H-acridin-2-one (VII) in 4.0 mL glacial acetic acid (HOAc) was treated with an excess of 37% peracetic acid and warmed in a 60° C. bath. The reaction was followed by tlc (silica gel plates developed with acetone/CHCl$_3$ [15:85, v/v]solvent) and was cooled when the starting material had been consumed. The reaction was evaporated to dryness in vacuo and the residue chromatographed on 100 g silica gel (230–400 mesh ASTM) packed in a 3 cm ID column and developed with acetone/CHCl$_3$ (4:96, v/v) solvent. The major product band was collected, freed of solvent in vacuo and crystallized from a minimum of boiling EtOAc to afford 28.4 mg (10.5%) of the title compound as shiny black crystals.

Analysis

IR (CHCl$_3$) cm$^{-1}$ 3001, 1611, 1594, 1488, 1468, 1445, 1411, 1371, 1294, 1248; $^1$H NMR (CDCl$_3$) δ8.27 (d, J=9.1Hz, 1H), 8.23 (d, J=9.7Hz, 1H), 7.05 (d, J=2.6Hz, 1H), 7.00 (d of d, J$_A$=9.1 HZ and J$_B$=2.6 Hz, 1H), 6.68–6.77 (m, 2H), 3.94 (s, 3H), 1.69 (s, 6H); $^{13}$C NMR (CDCl$_3$) ppm 185.9, 162.6, 147.2, 141.4, 136.1, 132.7, 130.7, 128.5, 123.7, 123.1, 113.1, 111.6, 55.8, 36.2, 32.9.

EXAMPLE II

Evaluation of Mediators

Graphite rod electrodes (3 mm in diameter from Johnson Matthey Electronics, Ward Hill, Mass.) were prepared by polishing the electrode's surface using first a fine grit sandpaper and then a suspension of ≦1 micron alumina particles. A 1 mM methanolic solution of the mediator was prepared and the electrode was soaked in this solution for 2 minutes. The electrodes were then rinsed with water and soaked for a short time in 0.25 M phosphate buffer (pH 7). At this point, a current -vs- voltage profile was run to determine the cathodic and anodic peak positions -vs- Ag/AgCl reference electrodes. Currents were then measured in pH=7 solutions containing NADH in concentrations from 20 to 200 μM, using a potential that was typically 100 mv more positive than the oxidation peak, and the slope of the line obtained from a least squares fit of the current -vs- NADH concentration data gave the relative sensitivity of each mediator in μA/μM NADH. These relative sensitivities are listed in Table I.

TABLE I

| Mediator | Relative Sensitivity μA/μM NADH |
| --- | --- |
| III (3-NTBO) | 0.0095 |
| I | 0.0032 |
| IV | 0.0027 |
| V | 0.002 |
| VI | 0.0012 |
| VII | 0.0009 |
| VIII | 0.0022 |
| IX | 0.0030 |

The relative sensitivity of the listed compounds can be interpreted as a gauge of the reactivity of the mediator with NADH or NADPH. The higher the value that is reported the more reactive the mediator is towards NADH or NADPH. All of these compounds would be useful as mediators in the previously described biosensor system because they provide sensitivity above the lower limit for such utility of 0.0009 μA/μM. This is the lower limit because at lower levels the response to NADH cannot be distinguished from the background.

EXAMPLE III

Figure 2:
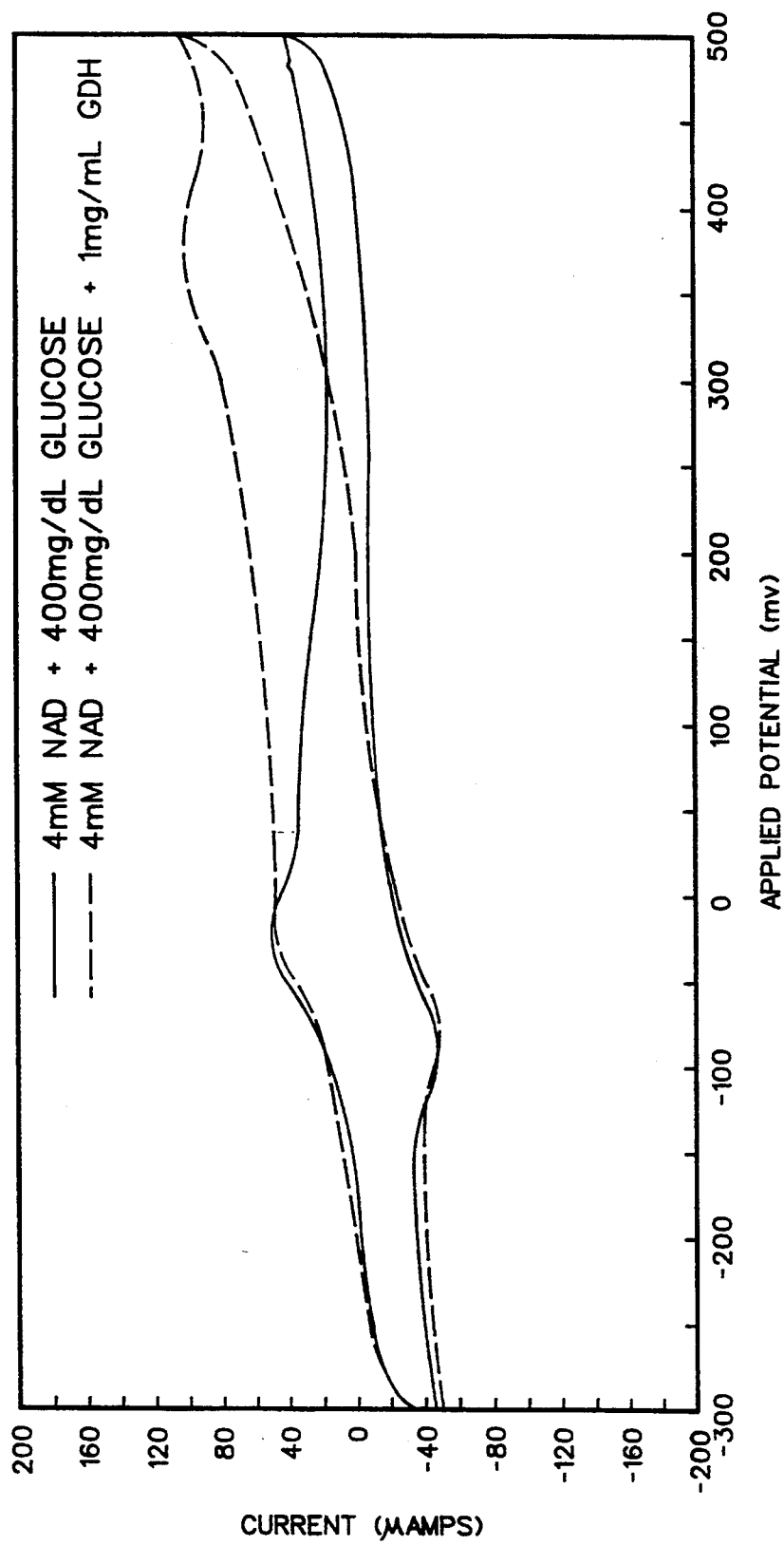

Compound I, 7-hydroxy-9,9-dimethyl-9H-acridin-2-one (DMA) was absorbed onto a graphite electrode of the type used in Example I from its 2 mM methanolic solution. Two test solutions containing a 2 mM methanolic solution of DMA were prepared whereupon the electrode was placed into the solution and scanned using cyclic voltammetry at 100 mV/sec. to find the catalytic wave. In the first test solution, NADH was introduced in increasing amounts up to a concentration of 3 mM. A wave between 300–400 mV versus Ag/AgCl appears. This wave which represents the oxidation of the reduced mediator is represented in FIG. 1. In a second experiment, 4 mM NAD+400 mg/dL glucose were used as a control. A small amount of glucose dehydrogenase (GDH) (1 mg/ml) was then introduced. The same wave that appeared in the NADH only experiment also is observed (FIG. 2). This confirms the utility of DMA as a mediator because NADH produced via the enzymatic reaction is present in a high enough concentration to be detected.

EXAMPLE IV

Figure 3:
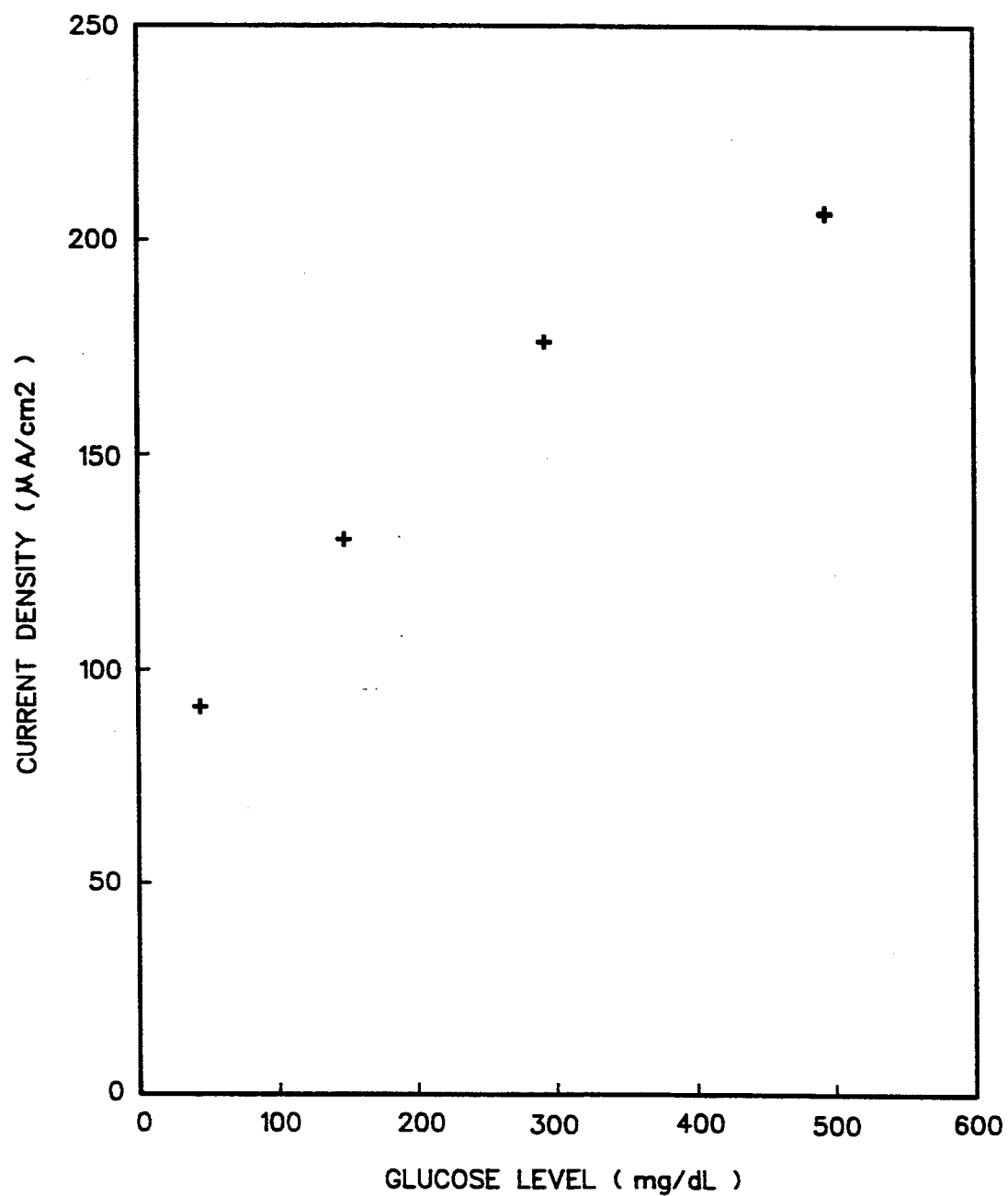

Experiments involving printed electrodes comprising a printed sensor card with a graphite/carbon working electrode and a silver/silver chloride reference electrode were carried out. The working electrode was treated with GDH enzyme by way of a 75 mg GDH per gram of polymer solution formulation (2% hydroxypropylmethyl-cellulose in H$_2$O ) from a pipette and dunked in a bath of 5 mM DMA in methanol for 4 minutes to introduce the mediator to the electrode whereupon it was removed and dried. The electrode was assembled in a format having a small capillary gap, treated with a 1 mM NAD+/glucose solution in buffer (100 mM $PO_4=$/100 mM KCl) and the current was measured with a potential of +0.6 V versus Ag/AgCl. The current density as a function of glucose level is graphically illustrated in FIG. 3 from which it can be determined that the sensor prepared using the mediator of the present invention provides a suitable dose response relationship when used in a biosensor system of the type under consideration.

What is claimed is:

1. An electrode having a surface used for electrochemical regeneration of coenzymes dihydronicotinamide adenine dinucleotide (NADH), dihydronicotinamide adenine dinucleotide phosphate (NADPH) or analogs thereof characterized in that there has been imparted to the electrode surface a mediator function comprising one or more mediator compounds selected from the group consisting of substituted or unsubstituted 9H-acridin-2-ones and 11H-dibenz[b,e][1,4,]oxazepine-2-ones.

2. An electrode as characterized by claim 1 wherein the mediator is characterized by the formula:

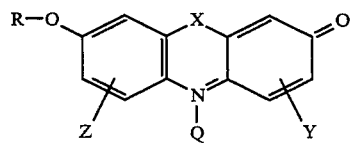

wherein X is

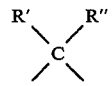

where R' and R" are lower alkyl of 1 to 6 carbon atoms or

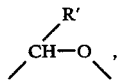

Y and Z are independently H or another monovalent substituent, Q is $(\rightarrow O)_n$ where n=0 or 1 and R is H or lower alkyl of 1 to 6 carbon atoms.

3. The electrode of claim 2 wherein Y and Z are independently hydrogen, substituted or unsubstituted aryl, alkoxy, aryloxy, halo, nitro, substituted amino, keto, carboxy, alkoxycarbonyl or amino.

4. The electrode of claim 1 wherein one or more enzyme are present at the electrode surface.

5. The electrode of claim 4 wherein the enzyme is a dehydrogenase.

6. The electrode of claim 1 wherein the electrode is comprised of graphite, pyrolytic carbon, glassy carbon, platinum or gold.

7. The electrode of claim 1 wherein the mediator compound is 7-hydroxy-9,9-dimethyl-9H-acridin-2-one.

8. A method of improving the performance of a biochemical fuel cell which operates with dehydrogenase as a catalyst and a co-enzyme as an energy-transferring redox couple, which method involves using the electrode described in claim 1 as an anode in said fuel cell.

9. The method of claim 8 wherein the mediator compound is:

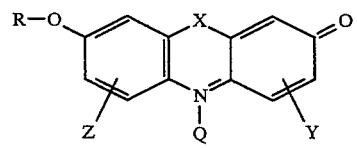

wherein X is

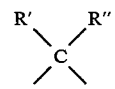

where R' and R" are lower alkyl of 1 to 6 carbon atoms or

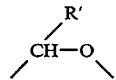

Y and Z are independently H or another monovalent substituent, Q is $(\rightarrow O)_n$ where n=0 or 1 and R is H or lower alkyl of 1 to 6 carbon atoms.

10. The method of claim 8 wherein the electrode is comprised of graphite, pyrolytic carbon, glassy carbon, platinum or gold and the mediator compound is 7-hydroxy-9,9-dimethyl-9H-acridin-2-one.

* * * * *